United States Patent
Rajagopalan (10) Patent No.: US 8,367,655 B2
(45) Date of Patent: Feb. 5, 2013

(54) PYRIDOINDOLOBENZOX—AND THIAZEPINE DERIVATIVES AND USES THEREOF

(75) Inventor: Parthasarathi Rajagopalan, St. Peters, MO (US)

(73) Assignee: Daya Drug Discoveries, Inc., St. Louis, MO (US)

( * ) Notice: Subject to any disclaimer, the term of this patent is extended or adjusted under 35 U.S.C. 154(b) by 305 days.

(21) Appl. No.: 12/803,701

(22) Filed: Jul. 2, 2010

(65) Prior Publication Data

US 2011/0003840 A1   Jan. 6, 2011

Related U.S. Application Data

(60) Provisional application No. 61/270,093, filed on Jul. 3, 2009.

(51) Int. Cl.
  *A61P 25/18* (2006.01)
  *A61K 31/55* (2006.01)
  *C07D 267/02* (2006.01)
  *C07D 281/08* (2006.01)

(52) U.S. Cl. .................................. 514/211.1; 540/546

(58) Field of Classification Search ............ 514/211.1; 540/546
See application file for complete search history.

(56) References Cited

U.S. PATENT DOCUMENTS

| | | |
|---|---|---|
| 3,790,674 A | 2/1974 | Blumberg |
| 3,983,123 A | 9/1976 | Adams |
| 4,438,120 A | 3/1984 | Rajagopalan |
| 5,321,023 A | 6/1994 | Rajagopalan |

*Primary Examiner* — Brenda Coleman
(74) *Attorney, Agent, or Firm* — Raghavan Rajagopalan (57) ABSTRACT

The present invention discloses pyridoindolobenzox- and thiazepine compositions of Formula 1, wherein

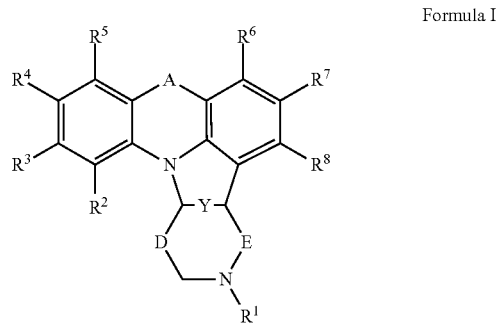

Formula I A is —CH($R^9$)—X—, —XCH($R^9$)—; —CO—X— or —X—CO—; X is —O—, —S—, —SO—, or —SO$_2$—. Y is a single bond or a double bond. D and E are independently —(CH$_2$)$_n$—; and 'n' varies from 0 to 2. $R^1$ to $R^9$ are various electron donating, electron withdrawing, hydrophilic, or lipophilic groups selected to optimize the physicochemical and biological properties of compounds of Formula I.

28 Claims, 4 Drawing Sheets

Fig. 1. Synthesis of Pyridoindolodibenzothiazepines

Fig. 2. Synthesis of Pyridoindolodibenzoxazepine

Fig. 3. X-Ray crystal structure of compound 2.

Data table

| Treatment Group | Horizontal Activity | Total Distance (cm) |
|---|---|---|
| Vehicle 1ml/kg + Amph 1mg/kg (N=6) | 9,237 ± 1,659 | 3,379±792 |
| DDD-016 3mg/kg + Amph 1mg/kg (N=6) | 11,532 ± 1,632 | 4,348±1,000 |
| DDD-016 10mg/kg + Amph 1mg/kg (N=4) | 4,600 ± 1,491* | 1,838±567 |

Fig. 4. Prepulse inhibition data using the indolobenzothiazepine compound 7.

PYRIDOINDOLOBENZOX—AND THIAZEPINE DERIVATIVES AND USES THEREOF

This application claims benefit of priority based on prior provisional application No. 61/270,093 filed on Jul. 3, 2009.

This invention was made with U.S. Government support from the National Institute of Mental Health (NIMH) of National Institutes of Health, under the Small Business Innovation Research (SBIR) Phase I Grant No. 1 R43MH084365. In accordance with the Federally Sponsored Research or Development, the U.S. Government has certain rights to this invention.

FIELD OF INVENTION

This invention relates to novel pyridoindolobenzox- and thiazepine derivatives for the treatment of schizophrenia and other central nervous system (CNS) disorders.

PRELIMINARY NOTE

Various prior art references in the specification are indicated by italicized Arabic numerals in brackets. Full citation corresponding to each reference number is listed at the end of the specification, and is herein incorporated by reference in its entirety in order to describe fully and clearly the state of the art to which this invention pertains.

Unless otherwise specified, all technical terms and phrases used herein conform to standard organic and medicinal chemistry nomenclature established by International Union of Pure and Applied Chemistry (IUPAC), American Chemical Society (ACS), and other international professional societies. The rules of nomenclature are described in various publications, including "Nomenclature of Organic Compounds" [1], and "Systematic Nomenclature of Organic Chemistry" [2], which are herein incorporated by reference in their entireties.

BACKGROUND

CNS disorders comprise several major categories as described in the Diagnostic and Statistical Manual of Mental Disorders (DSM IV-TM) [3]. Psychotic disorders include schizophrenia, paranoia, and manic-depressive illness. Motor disorders include Parkinson's disease, epilepsy, and Tourette's syndrome. Mood disorders include depression, mania, and bipolar disorder. Anxiety disorders include generalized anxiety, phobias, panic attacks, and obsessive compulsive disorders. Cognitive disorders include autism, mild cognitive impairment (MCI), Attention Deficit Hyperactivity Disorder (ADHD), and dementia. Substance-related disorders include narcotic addiction and withdrawal; and eating disorders such as Anorexia Nervosa, bulimia, and obesity. Other disorders involving CNS include sleep disorders, endocrine disorders, or pain.

It is well established that a particular CNS disorder may involve complex interactions of multiple neuroreceptors and neurotransmitters, and, conversely, a single neuroreceptor may be implicated in several CNS disorders as exemplified by the serotonin (5-hydroxytryptamine or "5-HT") and dopamine (3,4-dihydroxyphenyl-ethylamine or "D") systems outlined in Table 1. Many of the receptors that are distributed in the brain are also found in other areas of the body including gastrointestinal (GI) tract, blood vessels, and muscles, and elicit physiological response upon activation by appropriate ligands.

TABLE 1

Receptor Subtypes, Distribution, and Associated CNS Disorders.

| Receptor | Implicated Disorders |
|---|---|
| Sertotonin | |
| $5\text{-}HT_{1A}$ | Addiction, aggression, anxiety, appetite, memory, mood, erectile dysfunction, sexual behavior, sleep, sociability. |
| $5\text{-}HT_{1B}$ | Addiction, aggression, anxiety, learning, memory, mood, penile erection, sexual behavior. |
| $5\text{-}HT_{1D}$ | Anxiety, locomotion, vasoconstriction. |
| $5\text{-}HT_{1E}$ | Unknown. |
| $5\text{-}HT_{1F}$ | Vasoconstriction. |
| $5\text{-}HT_{2A}$ | Addiction, anxiety, appetite, cognition, learning, memory, mood, perception, psychosis, sexual behavior, sleep. |
| $5\text{-}HT_{2B}$ | Addiction, anxiety, appetite, GI motility, sleep, vasoconstriction. |
| $5\text{-}HT_{2C}$ | Addiction, anxiety, appetite, GI motility, locomotion, mood, perception, penile erection, sexual behavior, sleep. |
| $5\text{-}HT_3$ | Addiction, anxiety, GI motility, learning, memory, nausea. |
| $5\text{-}HT_4$ | Addiction, anxiety, GI motility, learning, memory, mood, respiration. |
| $5\text{-}HT_{5A}$ | Locomotion, sleep. |
| $5\text{-}HT_6$ | Anxiety, cognition, learning, memory, mood. |
| $5\text{-}HT_7$ | Anxiety, memory, mood, respiration, sleep. |
| Dopamine | |
| $D_1$ | Addiction, ADHD, autism, bipolar disorder, dissociative disorder, depression, eating disorder, impulse control disorder, obesity, obsessive compulsive disorder, Parkinson's disease, somatoform disorder. |
| $D_2$ | Addiction, bipolar disorder, depression, mania, Parkinson's disease, schizophrenia, tardive diskinesia. |
| $D_3$ | Addiction, ophthalmic disorders, schizophrenia. |
| $D_4$ | Bulimia, erectile dysfunction, schizophrenia. |
| $D_5$ | ADHD, autism, depression, dissociative disorder, eating disorder, impulse control disorder, movement disorder, obsessive compulsive disorder, somatoform disorder, tardive diskinesia,. |

The rational drug design process is based on the well established fundamental principle that receptors, antibodies, and enzymes are multispecific. Topologically similar molecules will have similar binding affinity to these biomolecules, and, therefore, are expected to elicit similar physiological response as those of native ligands, antigens, or substrates respectively. The aforementioned principle, as well as molecular modeling and quantitative structure activity relationship studies (QSAR) are quite useful for designing molecular scaffolds that target receptors in a "broad sense." However, they do not provide sufficient guidance for targeting specific receptor subtypes, wherein subtle changes in molecular topology could have substantial impact on receptor binding profile. Moreover, this principle is inadequate for predicting in vivo properties of any compound. Hence, each class of molecules should be evaluated in its own right not only for receptor subtype affinity and selectivity, but also for efficacy and toxicity profiles in in vivo animal models. Thus, there is a sustained need for the discovery and development of new drugs that target neuroreceptor subtypes with high affinity and selectivity in order to improve efficacy and/or minimize undesirable side effects.

Serotonin and dopamine constitute the two major neurotransmitters that are implicated in numerous disorders. To date, fourteen serotonin and five dopamine receptor subtypes have been isolated, cloned, and expressed. The present invention is directed at targeting the serotonin $5\text{-}HT_{2A}$ and $D_2$ receptor subtypes for the treatment of CNS disorders that may be implicated by these receptor subtypes, including schizophrenia (cf. Table 1). Schizophrenia is an insidious mental disorder that affects about 1% of the world population. In the United States, the economic and social impact of this disease is enormous, and the cost of hospitalization, treatment, and medications coupled with loss of employment exceeds 60 billion dollars [4]. Schizophrenia manifests itself in two distinct, complex, and diverse symptoms. Positive symptoms comprise hallucinations, delusions, incoherence of speech, passivity, withdrawal, and incongruity of emotions. The negative symptoms include poverty of speech, reduced emotional response, inability to feel intimacy or initiate social contacts, lack of motivation, underachievement at school or work, and attention impairment. The overall description of the positive symptoms, according to clinical psychiatrists, is that it is a distortion or exaggeration of normal behavior while negative symptoms represent a diminution or loss of normal function.

Schizophrenia has been postulated to be the result of neurotransmitter dysfunction. In particular, $5\text{-}HT_{2A}$ and the $D_2$ receptors have been the most implicated in the etiology of Schizophrenia. Drugs that target dopamine receptors are referred to as 'classical antispsychotics', and include chlorpromazine (Thorazine) and haloperidol (Serenace). A serious shortcoming associated with the dopamine hypothesis is the fact that a large percentage of the patients do not respond to the first-time treatment with such drugs. Therefore, an alternate neurotransmitter hypothesis, known as the 'serotonin hypothesis,' has been proposed, and the selective $5\text{-}HT_{2A}$ antagonist, ketanserin, has been effective in alleviating the negative symptoms of Schizophrenia [5]. Because the central dopaminergic and serotonergic pathways are connected anatomically, and interact functionally in the ventral tegmental and the prefrontal cortex areas of the brain implicated in schizophrenia, a combination serotonin receptor and dopamine receptor antagonist was found to alleviate both the positive and negative symptoms as well as movement disorders in schizophrenic patients [6-9]. This observation provided the impetus for the development of an integrated molecular entity (referred to as 'atypical antipyschotics) such as clozapine and olanzapine that target both $5\text{-}HT_{2A}$ and $D_2$ receptors. The serotonin-dopamine antagonist (SDA) hypothesis postulates moderate $D_2$ receptor blockade for the reduction of positive symptoms, and potent $5\text{-}HT_{2A}$ receptor blockade for attenuation of the negative symptoms and movement disorders.

Rajagopalan [10, 11] disclosed pyridoindolobenzodiazepine derivatives A-H, but the compounds bearing other heteroatoms such as O, S, SO, or $SO_2$ instead of NH in the B ring belong to novel heterocyclic systems that have not been disclosed before. The carbon analogs ($X=CH_2$) in the B-ring of A-H have been disclosed by Adams and De Witt [12, 13].

A: X = CH₂
B: X = NH

C: X = CH₂
D: X = NH

E: X = CH₂
F: X = NH

G: X = CH₂
H: X = NH

Moreover, as mentioned before, the receptor binding and pharmacological properties are very sensitive to the overall molecular topology, and these properties cannot be readily predictable just from the molecular structure. For example, the regioisomers A,C and B,D as well as their corresponding cis- and trans-reduced analogs E,F and G,H in both azepine and diazepine systems display different receptor binding profiles and activities.

SUMMARY

The present invention discloses pentacyclic compounds of Formula I,

Formula I wherein A is —CH($R^9$)—X—, —XCH($R^9$)—; —CO—X— or —X—CO—; X is —O—, —S—, —SO—, or —$SO_2$—. Y is a single bond or a double bond. D and E are independently —(CH₂)$_n$—, and 'n' varies from 0 to 2. $R^1$ to $R^9$ are various electron donating, electron withdrawing, hydrophilic, or lipophilic groups selected to optimize the physicochemical and biological properties of compounds of Formula I. These properties include receptor binding, receptor selectivity, tissue penetration, lipophilicity, toxicity, bioavailability, and pharmacokinetics. As will be evident from the sections that follow, some of the compounds of the present invention exhibit favorable in vivo biological properties that could not be ascertained from the prior art literature. Compounds of the present invention are useful for the treatment of individuals suffering from schizophrenia as well as other mental and peripheral disorders.

DETAILED DESCRIPTION

The present invention relates to pentacyclic compounds of Formula I, wherein

Formula I

A is —CH($R^9$)X—, —XCH($R^9$)—, —COX—, or —XCO—;
X is —O—, —S—, —SO—, or —$SO_2$—;
Y is a single bond or a double bond;
D and E are independently —$(CH_2)_n$—, and 'n' varies from 0 to 2;
$R^1$ is selected from the group consisting of hydrogen, $C_1$-$C_{10}$ alkyl, $C_1$-$C_{10}$ hydroxyalkyl, $C_5$-$C_{10}$ aryl unsubstituted or substituted with electron donating groups (EDG) or electron withdrawing groups (EWG), $C_6$-$C_{15}$ aroylalkyl, and $C_1$-$C_{10}$ alkxoycarbonylalkyl, $C_6$-$C_{10}$ arylalkyl unsubstituted or substituted with EDG or EWG;
$R^2$ to $R^9$ are independently selected from the group consisting of hydrogen, $C_1$-$C_{10}$ alkyl, hydroxyl, $C_1$-$C_{10}$ alkoxyl, —$NR^{10}R^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl unsubstituted or substituted with EDG or EWG, and $C_6$-$C_{10}$ arylalkyl unsubstituted or substituted with EDG or EWG; and
$R^{10}$ and $R^{11}$ are independently hydrogen or $C_1$-$C_{10}$ alkyl, and $R^{10}$ and $R^{11}$ may optionally be tethered together from rings.

The phrase, 'electron donating group (EDG)' and 'electron withdrawing group (EWG)' are well understood in the art. EDG comprises alkyl, hydroxyl, alkoxyl, amino, acyloxy, acylamino, mercapto, alkylthio, and the like. EWG comprises halogen, acyl, nitro, cyano, trihaloalkyl, carboxyl, alkoxycarbonyl, sulfonyl, and the like.

The first embodiment of the present invention is represented by Formula I, wherein
A is —CH($R^9$)X—;
X is —O—, —S—, —SO—, or —$SO_2$—;
Y is a single bond or a double bond;
D and E are —$(CH_2)_n$—, and 'n' is 1;
$R^1$ is selected from the group consisting of hydrogen, $C_1$-$C_{10}$ alkyl, $C_1$-$C_{10}$ hydroxyalkyl, $C_5$-$C_{10}$ aryl unsubstituted or substituted with electron donating or electron withdrawing groups, $C_1$-$C_{15}$ aroylalkyl, and $C_1$-$C_{10}$ alkxoycarbonylalkyl, $C_6$-$C_{10}$ arylalkyl unsubstituted or substituted with EDG or EWG;
$R^2$ to $R^9$ are independently selected from the group consisting of hydrogen, $C_1$-$C_{10}$ alkyl, hydroxyl, $C_1$-$C_{10}$ alkoxyl, —$NR^{10}R^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl unsubstituted or substituted with EDG or EWG, and $C_6$-$C_{10}$ arylalkyl unsubstituted or substituted with EDG or EWG; and
$R^{10}$ and $R^{11}$ are independently hydrogen or $C_1$-$C_{10}$ alkyl, and $R^{10}$ and $R^{11}$ may optionally be tethered together from rings.

The second embodiment is represented by Formula I, wherein
A is —XCH($R^9$)—;
X is —O—, —S—, —SO—, or —$SO_2$—;
Y is a single bond or a double bond;
D and E are —$(CH_2)_n$—, and 'n' is 1;
$R^1$ is selected from the group consisting of hydrogen, $C_1$-$C_{10}$ alkyl, $C_1$-$C_{10}$ hydroxyalkyl, $C_5$-$C_{10}$ aryl unsubstituted or substituted with electron donating or electron withdrawing groups, $C_6$-$C_{15}$ aroylalkyl, and $C_1$-$C_{10}$ alkxoycarbonylalkyl, $C_6$-$C_{10}$ arylalkyl unsubstituted or substituted with EDG or EWG;
$R^2$ to $R^9$ are independently selected from the group consisting of hydrogen, $C_1$-$C_{10}$ alkyl, hydroxyl, $C_1$-$C_{10}$ alkoxyl, —$NR^{10}R^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl unsubstituted or substituted with EDG or EWG, and $C_6$-$C_{10}$ arylalkyl unsubstituted or substituted with EDG or EWG; and
$R^{10}$ and $R^{11}$ are independently hydrogen or $C_1$-$C_{10}$ alkyl, and $R^{10}$ and $R^{11}$ may optionally be tethered together from rings.

The third embodiment is represented by Formula I, wherein
A is —CH($R^9$)X—;
X is —O—, —S—, —SO—, or —$SO_2$—;
Y is a single bond or a double bond;
D and E are —$(CH_2)_n$—, and 'n' is 1;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and
each of $R^4$ and $R^7$ are independently hydrogen, $C_1$-$C_{10}$ alkyl, or halogen.

The fourth embodiment is represented by Formula I, wherein
A is —XCH($R^9$)—;
X is —O—, —S—, —SO—, or —$SO_2$—;
Y is a single bond or a double bond;
D and E are —$(CH_2)_n$—, and 'n' is 1;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and
each of $R^4$ and $R^7$ are independently hydrogen, $C_1$-$C_{10}$ alkyl, or halogen.

Figure 1:
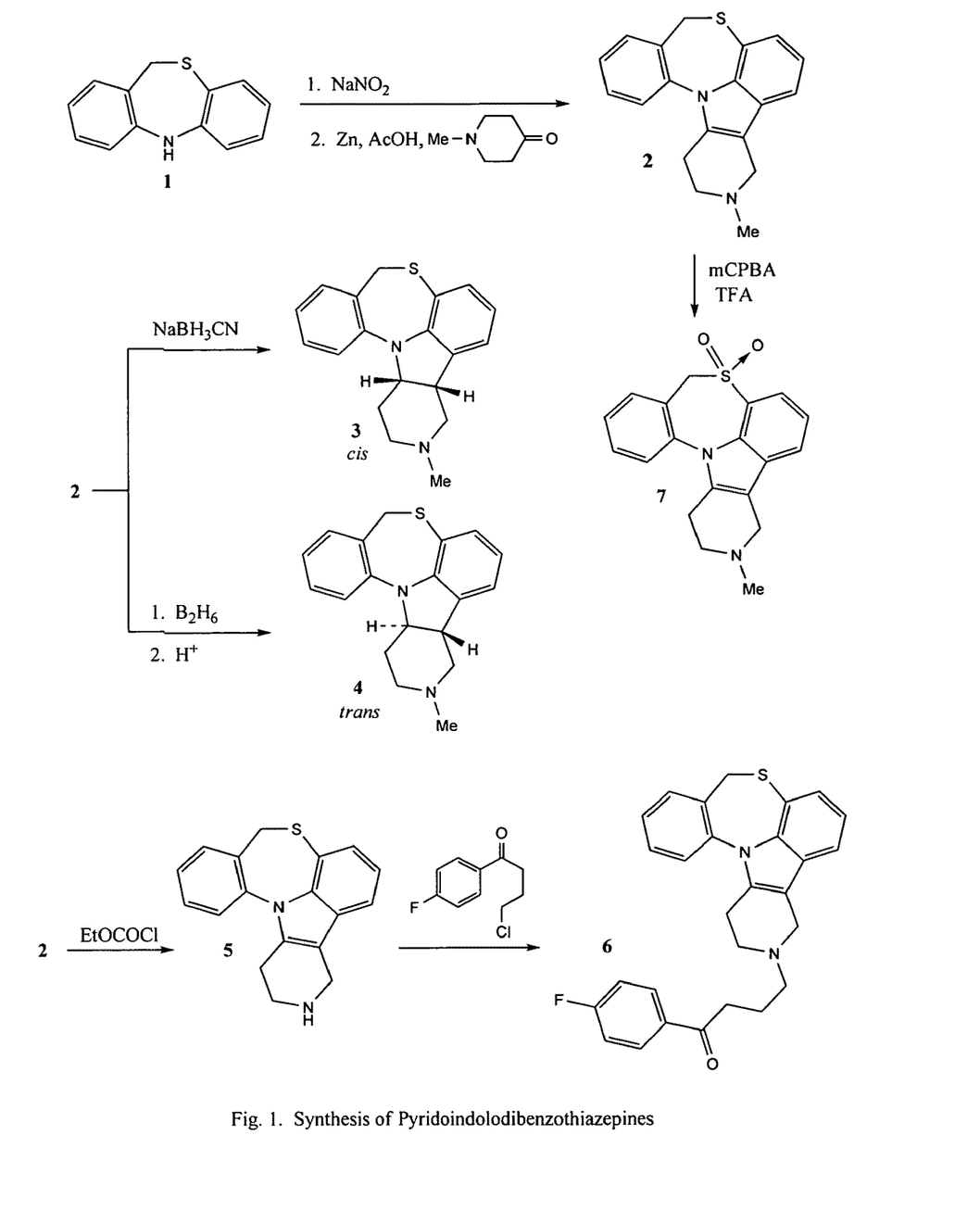
FIG. 1. Synthetic scheme for pyridindolobenzothiazepines.
Figure 2:
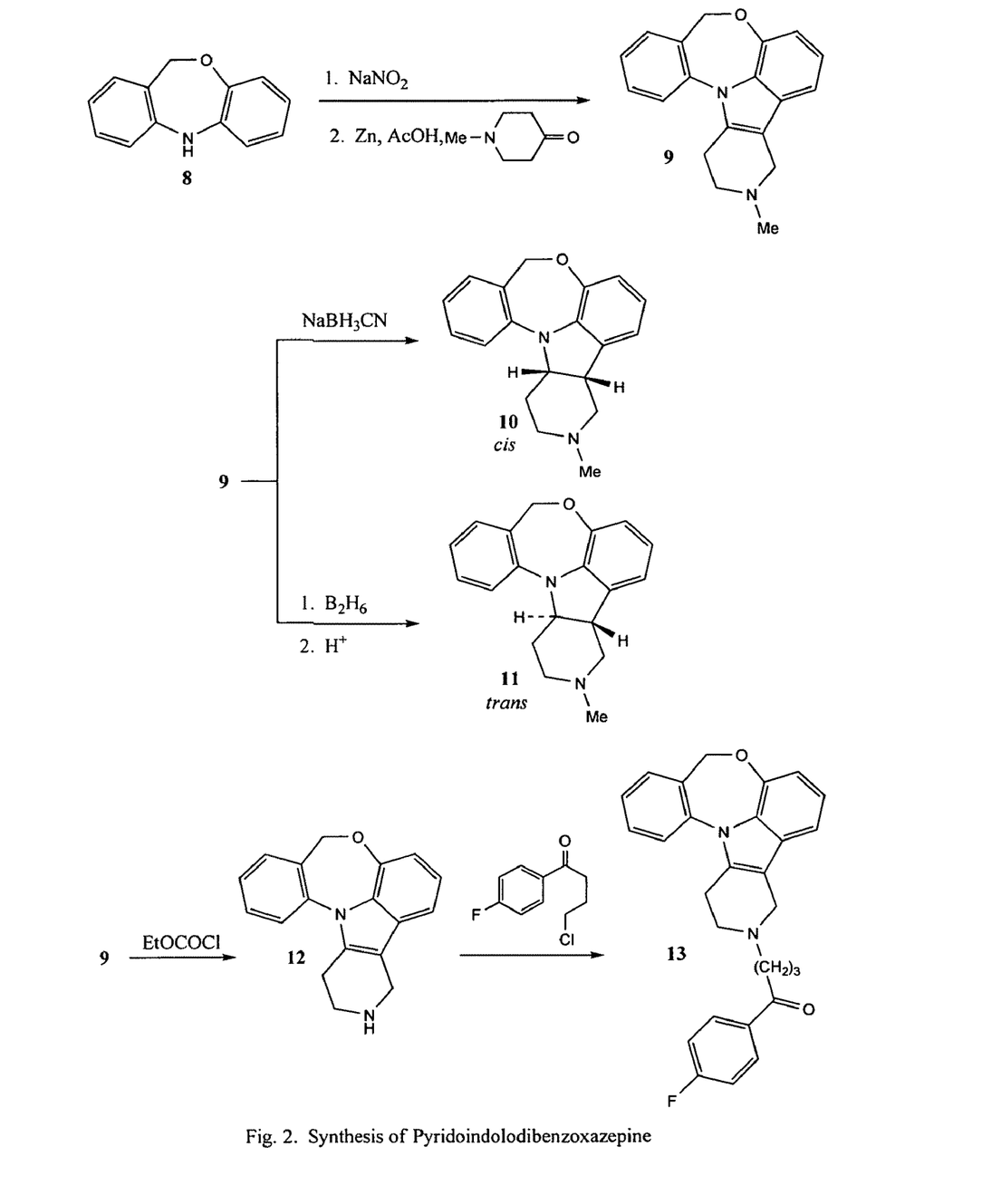
FIG. 2. Synthetic scheme for pyridoindolobenzoxazepines.

The compounds belonging to Formula I can be synthesized according to standard methods as outlined in FIGS. 1 and 2 starting from the known tricyclic dibenzoxazepine and dibenzothiazepine [14, 15]. Compounds of the present invention may exist as a single stereoisomer or as mixture of enantiomers and diastereomers whenever chiral centers are present. Individual enantiomers can be isolated by resolution methods or by chromatography using chiral columns. The diastereomers can be separated by standard purification methods such as fractional crystallization or chromatography. Compounds of the present invention may exist in the form pharmaceutically acceptable salts, including but not limited to acetate, adipate, citrate, tartarate, benzoate, phosphate, glutamate, gluconate, fumarate, maleate, succinate, oxalate, chloride, bromide, hydrochloride, sodium, potassium, calcium, magnesium, ammonium, and the like. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio.

The compounds of the present invention represented by Formula I, commonly referred to as 'active pharmaceutical ingredient (API)' or 'drug substance' is typically formulated with pharmaceutically acceptable salts, buffers, diluents, carriers, adjuvants, preservatives, and excipients. The formulation technology for manufacture of the drug product is known in the art, and are described in "Remington, The Science and Practice of Pharmacy" [16], incorporated herein by reference in its entirety.

The final formulated product, commonly referred to as 'drug product,' may be administered enterally, parenterally, or topically. Enteral route includes oral, rectal, topical, buccal, ophthalmic, and vaginal administration. Parenteral route includes intravenous, intramuscular, intraperitoneal, intrasternal, and subcutaneous injection or infusion. The drug product may be delivered in solid, liquid, or vapor forms, or can be delivered through a catheter for local delivery at a target. It may also be administered alone or in combination with other drugs if medically necessary.

Compositions suitable for parenteral injection may comprise physiologically acceptable, sterile aqueous or nonaqueous isotonic solutions, dispersions, suspensions or emulsions, and sterile powders for reconstitution into sterile injectable solutions or dispersions. The compositions may also optionally contain adjuvants such as preserving, wetting, emulsifying, dispensing, and antimicrobial agents. Examples of suitable carriers, diluents, solvents, vehicles, or adjuvants include water; alcohols such as ethanol, propyleneglycol, polyethyleneglycol, glycerol, and the like; vegetable oils such as cottonseed, groundnut, corn, germ, olive, castor and sesame oils, and the like; organic esters such as ethyl oleate and suitable mixtures thereof; and phenol, parabens, sorbic acid, and the like.

Injectable formulations may also be suspensions that contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the drug in biodegradable polymers. Depending upon the ratio of drug to polymer and the nature of the particular polymer employed, these compositions release the active ingredient(s) only, or preferentially, in a certain part of the intestinal tract, and optionally, in a delayed manner. Thus, the rate of drug release and the site of delivery can be controlled. Examples of embedding compositions include, but are no limited to polylactide-polyglycolide poly(orthoesters), and poly(anhydrides), and waxes. The technology pertaining to controlled release formulations are described in "Design of Controlled Release Drug Delivery Systems," [17] incorporated herein by reference in its entirety.

Formulations for oral administration include capsules (soft or hard), tablets, pills, powders, and granules. Such formulations may comprise the API along with at least one inert, pharmaceutically acceptable ingredients selected from the following: (a) buffering agents such as sodium citrate or dicalcium phosphate; (b) fillers or extenders such as starches, lactose, sucrose, glucose, mannitol, and silicic acid; (c) binders such as carboxymethylcellulose, alginates, gelatin, polyvinylpyrrolidone, sucrose, and acacia; (d) humectants such as glycerol; (e) disintegrating agents such as agar-agar, calcium carbonate, potato or tapioca starch, alginic acid, certain silicates, and sodium carbonate; (f) solution retarding agents such as paraffin; (g) absorption accelerators such as quaternary ammonium compounds; (h) wetting agents such as cetyl alcohol and glycerol monostearate; (i) absorbents such as kaolin and bentonite clay and (j) lubricants such as talc, calcium stearate, magnesium stearate, solid polyethylene glycols, sodium lauryl sulfate, and mixtures thereof; (k) coatings and shells such as enteric coatings, flavoring agents, and the like.

Liquid dosage forms for oral administration include pharmaceutically acceptable emulsions, solutions, suspensions, syrups and elixirs. In addition to the API, the liquid dosage forms may contain inert diluents, solubilizing agents, wetting agents, emulsifying and suspending agents, sweetening, flavoring, and perfuming agents used in the art. Formulations for topical administration include powders, sprays, ointments and inhalants.

These formulations include the API along with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art and are described in "Liposomes," [18], which is incorporated herein by reference in its entirety.

The compounds of the present invention can also be administered to a patient in the form of pharmaceutically acceptable 'prodrugs.' Prodrugs are generally used to enhance the bioavailability, solubility, in vivo stability, or any combination thereof of the API. They are typically prepared by linking the API covalently to a biodegradable functional group such as a phosphate that will be cleaved enzymatically or hydrolytically in blood, stomach, or GI tract to release the API. A detailed discussion of the prodrug technology is described in "Prodrugs: Design and Clinical Applications," [19] incorporated herein by reference.

The dosage levels of API in the drug product can be varied so as to achieve the desired therapeutic response for a particular patient. The phrase "therapeutically effective amount" of the compound of the invention means a sufficient amount of the compound to treat disorders, at a reasonable benefit/ risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated; the severity of the disorder; activity of the specific compound employed; the specific composition employed; age, body weight, general health, sex, diet of the patient; the time of administration; route of administration; and rate of excretion of the specific compound employed; and the duration of the treatment. The total daily dose of the compounds of this invention administered may range from about 0.0001 to about 1000 mg/kg/day. For purposes of oral administration, more preferable doses can be in the range from about 0.001 to about 5 mg/kg/day. If desired, the effective daily dose can be divided into multiple doses for optimal therapeutic effect.

The following examples illustrate specific embodiments and utilities of the invention, and are not meant to limit the invention. As would be apparent to skilled artisans, various modifications in the composition, operation, and method are possible, and are contemplated herein without departing from the concept and scope of the invention as defined in the claims.

Example 1

Synthesis of a Compound of Formula I, Wherein A is —CH$_2$X—; X is —S—; Y is Double Bond; D and E are —CH$_2$—; R$^1$ is Methyl; R$^2$-R$^9$ are Hydrogens (2)

2

Step 1. To a well stirred solution of compound 1 (6.98 g, 32.7 mmol) in THF (30 mL) and AcOH (9 mL), a concentrated solution of NaNO$_2$ (7.03 g, 101.9 mmol) in water (12 mL) was added dropwise at ambient temperature. The reaction was stirred at ambient temperature for 20 min and treated with water (100 mL). The product was filtered, washed with water, and dried to give 7.67 g (97%) of the nitroso compound.

Step 2. To a stirred solution of nitroso compound from step 1 (14.6 g, 61.1 mmol) and N-methyl 4-pyridone (9.04 g, 79.9 mmol) in ethanol (150 mL) and acetic acid (20 mL) at 55° C., was added zinc dust (12.0 g, 183.5 mmol) in three equal portions allowing 10 mins between the additions. The reaction was stirred for another 5 minutes and filtered hot. The solid washed with ethanol, and the resultant solution was heated to reflux for 30 minutes, and thereafter the solvent was removed in vacuo. The residue was treated with 8 mL of acetic acid, and heated to reflux for about 16 hours. The solvent was removed in vacuo and the residue was dissolved in methylene chloride (500 mL). The solid impurity was removed by filtration, and the filtrate was washed with 10% NaOH solution. The combined organic layer was washed with water and brine, dried over anhydrous sodium sulfate, filtered an the filtrate taken to dryness in vacuo. The crude product was purified by flash chromatography on silica gel using 0-5% MeOH/chloroform as the eluent to give 3.0 g (16%) of the desired product 2. LRMS: m/Z, 307 (M+H$^+$).

Example 2

Synthesis of a Compound of Formula I, cis isomer Wherein A is —CH$_2$X—; X is —S—; Y is Single Bond; D and E is —CH$_2$—; R$^1$ is Methyl; R$^2$-R$^9$ are Hydrogens (3)

3 cis

To a cold solution of compound 2 from Example 1 (0.50 g, 1.63 mmol) in trifluoroacetic acid (6.5 mL) at −5° C., was carefully treated with solid sodium cyanoborohydride (0.125 g, 1.99 mmol). The reaction mixture was then stirred at ambient temperature for 3 h, treated with 6N HCl solution, and heated under reflux for 30 minutes. The solution was cooled to ambient temperature, and excess trifluoroacetic acid was removed in vacuo. The residue was made alkaline treated with the treatment of 25% NaOH solution (10 mL), and the product extracted with chloroform. The combined organic layer was washed with water and brine, and dried over anhydrous sodium sulfate, filtered, and the filtrate evaporated in vacuo. The crude compound was purified by flash column chromatography on silica gel using 0-5% MeOH/Chloroform as the eluent to furnish 0.270 g (54%) of the cis isomer 3. LRMS: m/Z, 309 (M+H$^+$).

Example 3

Synthesis of a Compound of Formula I, Trans Isomer Wherein A is —CH$^2$X—; X is —S—; Y is Single Bond; D and E is —CH$_2$—; R$^1$ is Methyl; R$^2$-R$^9$ are Hydrogens (4)

4 trans

The compound 2 from Example 1 (0.306 g, 1 mmol) was treated with borane-THF (10 mL, 1.0 M) at ambient temperature, and the mixture was heated under reflux for 1 hour by which time the reaction mixture became clear. After cooling to ambient temperature, the solution was treated with water to quench excess reagent borane reagent. The solvents were removed under reduced pressure, and the residue was treated with conc. HCl (7 mL). The mixture was heated to reflux for 3 hours and evaporated to dryness in vacuo, and treated with 10% NaOH solution (10 mL). The product was then extracted with EtOAc, washed with water and brine, dried over anhydrous sodium sulfate, filtered, and the filtrate taken to dryness under reduced pressure. The crude product was purified by flash chromatography on silica gel using 0-5% MeOH/Chloroform as the eluent to give 0.202 g (66%) of the trans isomer 4. LRMS: m/Z, 309 (M+H$^+$).

Example 4

Single Crystal X-Ray Structure Determination of Compound 4

Figure 3:
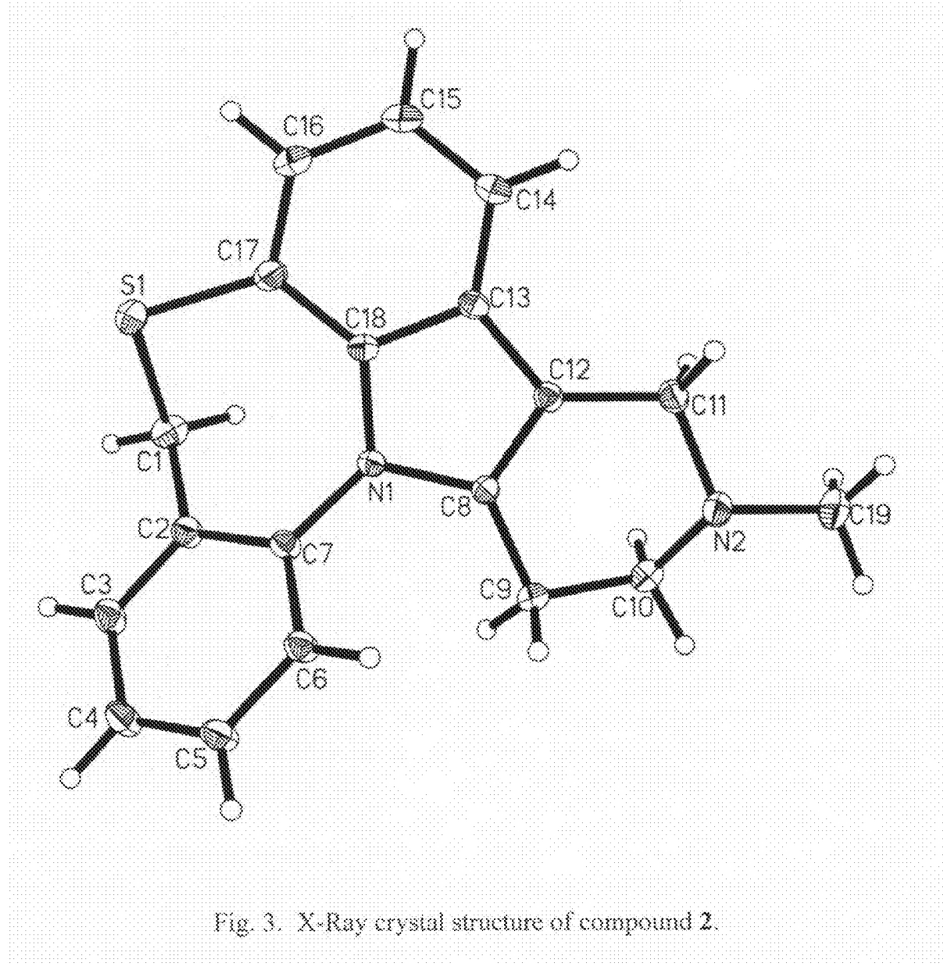
FIG. 3. X-Ray crystallographic structure of pyridoindolobenzothiazepine 2.

A sample of compound 4 was dissolved in methanol and allowed to cool slowly to give X-ray-quality crystals. The Projection Diagram shown in FIG. 3 confirms the structure of 2 as designated.

Example 5

Synthesis of a Compound of Formula I, Wherein A is —CH$_2$X—; X is —S—; Y is Double Bond; D and E is —CH$_2$—; R$^2$-R$^9$ are Hydrogens (5)

5

The unsaturated compound 4 from Example 1 (1.0 mmol) was dissolved in methylene chloride (5 mL), and was treated with ethyl chloroformate ( ). The reaction mixture was stirred at ambient temperature for 24 hours. After complete decomposition, the solution was poured onto 1N sodium hydroxide, and extracted with methylene chloride. The combined organic extracts were washed with brine, dried over anhydrous sodium sulfate, filtered, and the filtrate evaporated in vacuo to give the crude material, which was then purified by silica gel flash chromatography to give the desmethyl compound 7. LRMS: m/Z, 293 (M+H$^+$).

Example 6

Synthesis of a Compound of Formula I, Wherein A is —CH$_2$X—; X is —S—; Y is Double Bond; D and E is —CH$_2$—; R$^1$ is 3-(4-Fluorobenzoyl)Propyl; R$^2$-R$^9$ are Hydrogens

6

To a solution of 12 (0.292 g, 1.00 mmol) and 4-chloro-4'-fluoro-butyrophenone (0.216 g, 1.08 mmol) in DMF, was added sodium ioide (0.150 g, 1.00 mmol) followed by triethylamine (0.15 mL, 1.16 mmol). The reaction was heated under reflux for 3 hours. The reaction mixture was poured onto water and extracted with ethyl acetate. The combined organic layers were washed with water and brine, dried over anhydrous sodium sulfate, filtered, and the filtrate evaporated in vacuo. The crude compound was purified by flash chromatography. LRMS: m/Z, 457 (M+H$^+$).

Example 7

Synthesis of a Compound of Formula I, Wherein A is —CH$_2$X—; X is —SO$_2$—; Y is Double Bond; D and E is —CH$_2$—; R$^1$ is Methyl; R$^2$-R$^9$ are Hydrogens (7)

7

A solution of the thioether derivative in Example 3, (0.75 g, 2.4 mmol) in methylene chloride (20 mL) is cooled to 0° C., treated with trifluoroacetic acid (0.89 g, 7.8 mmol), and stirred at this temperature for about 30 minutes. Thereafter, 3-chloroperoxybenzoic acid (1.26 g 7.3 mmol) was added and the entire mixture was stirred at ambient temperature for 1 hour by which time the dark green solution turned into an orange slurry. The reaction mixture was then poured onto water (100 mL) and treated with 10% sodium hydroxide solution (30 mL). The organic layer was separated, washed with water, dried over anhydrous sodium sulfate, filtered, and the filtrated evaporated in vacuo. The greenish-yellow residue was purified by flash chromatography to give the desired sulfone 7. LRMS: m/Z, 339 (M+H$^+$).

Example 8

Synthesis of a Compound of Formula I, Wherein A is —CH$_2$X—; X is —O—; Y is Double Bond; D and E is —CH$_2$—; R$^1$ is Methyl; R$^2$-R$^9$ are Hydrogens (9)

9

Synthesis of the oxazepine derivative 9 was prepared by nearly the same procedure as the one used for the preparation of the thiazepine analog 2 in Example 1.

Step 1. To a well stirred solution of compound 8 (7.10 g, 36 mmol) in ethanol (200 mL) and glacial acetic acid (25 mL), a concentrated solution of NaNO$_2$ (11.00 g, 159 mmol) in water (13 mL) was added dropwise at ambient temperature. The reaction was stirred at ambient temperature for 20 min and treated with water (100 mL). The product was filtered, washed with water, and dried to give 6.5 g (80%) of the nitroso compound.

Step 2. To a stirred mixture of nitroso compound from step 1 (5.62 g, 24.9 mmol) and N-methyl 4-pyridone (3.66 g, 32.4 mmol) in ethanol (125 mL) and acetic acid (22 mL) at –20° C., was added zinc dust (4.88 g, 74.63 mmol) in three equal portions allowing 10 mins between the additions. The reaction was stirred for another 30 minutes and filtered hot. The solid washed with ethanol, and the resultant solution was treated with acetic acid (15 mL) and heated to reflux for 16 hours. Thereafter the solvent was removed in vacuo. The residue was treated with 8 mL of acetic acid, and heated to reflux for about 16 hours. The solvent was removed in vacuo, and the residue was dissolved in methylene chloride-ether (1:2 v/v) (500 mL). The solid impurity was removed by filtration, and the filtrate was washed with 10% NaOH solution. The combined organic layer was washed with water and brine, dried over anhydrous sodium sulfate, filtered and the filtrate taken to dryness in vacuo. The crude product was purified by flash chromatography on silica gel using 0-5% MeOH/chloroform as the eluent to give 0.4 g of the desired product 9. LRMS: m/Z, 291 (M+H$^+$).

Example 9

In Vitro Serotonin and Dopamine Receptor Binding Results

The IC$_{50}$ values for 5-HT$_{2A}$, 5-HT$_{2C}$, and D$_2$ receptors are shown in Table 1. All the compounds tested showed excellent receptor binding activity with compound 4 being the most potent amongst all.

TABLE 1

Serotonin and dopamine receptor binding of compounds of Formula 1.

| Compound | IC$_{50}$ (nM) | | |
| --- | --- | --- | --- |
| | 5-HT$_{2A}$ | 5-HT$_{2C}$ | D$_2$ |
| 2 | 1 | 10 | 80 |
| 3 | 5 | 15 | 500 |
| 4 | 3 | 5 | 20 |
| 6 | 5 | 80 | 8 |
| 9 | 8 | 50 | 500 |

Example 10

In Vivo Behavioral Studies: Compound 4 Effects on Amphetamine-Induced Locomotion and Prepulse Inhibition Doses of compound 2 for these studies were selected from a pilot study that revealed robust catalepsy (without a loss of right reflex) with 30 mg/kg ip DDD-016. Some locomotor reduction was seen with 10 mg/kg, and 3 mg/kg did not differentiate from vehicle (75% DMSO; pilot study data not shown). The in vivo data are shown in FIG. 4.

Figure 4:
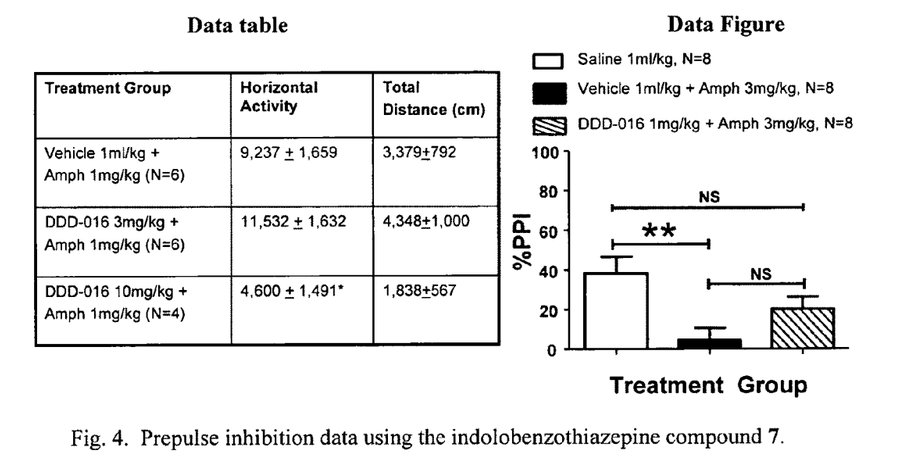
FIG. 4. In vivo rat schizophrenia model study: prepulse inhibition data.

Effects of compound 2 on amphetamine-induced motor activity (FIG. 4 Graph). All rats were habituated to the motor box for 30 min followed by injection of compound 2 or vehicle. After 30 min all rats were injected with 1 mg/kg, i.p. amphetamine (a dose that is known to elevate locomotion in rats) and their motor activity was recorded for 2 hr. Even with the small sample size, there is a trend for 10 mg/kg of 2 to reduce the effects of amphetamine. ANOVA with post hoc Newman Keuls revealed a difference between 3 mg/kg and 10 mg/kg of 2 for horizontal activity (p<0.05).

Effects of compound 2 on amphetamine-induced sensorimotor gating deficits (FIG. 4 Table). Once the compound 2 dose range was determined by motor assessments, a separate group of rats were used to study PPI. Rats were treated with vehicle (75% DMSO) or DDD-016 in the DMSO vehicle; 30 min later amphetamine (3 mg/kg ip) or saline was administered, and the startle session was initiated after an additional 30 min. (The 3 mg/kg dose of amphetamine is sufficient to induced robust deficits in PPI; 1 mg/kg is subthreshold; data not shown.) Shown are startle data from a 120 dB pulse, preceded 100 ms by a 71 dB pre-pulse. Rats treated with compound 2 vehicle and amphetamine demonstrated a decrease in % PPI compared to saline pretreated rats. Compound 2 (1 mg/kg ip) blunted this deficit (ANOVA with post hoc Newman Keuls; p<0.01). A similar magnitude of the inhibitory effect was seen with 3 and 10 mg/kg of 2 (data not shown), suggesting that E$_{max}$ was obtained even with the 1 mg/kg dose.

REFERENCES

1. Fox, R. B.; Powell, W. H. *Nomenclature of Organic Compounds: Principles and Practice*, Second Edition. Oxford University Press, Oxford, 2001.

2. Hellwinkel, D. *Systematic Nomenclature of Organic Chemistry: A Directory of Comprehension and Application of its Basic Principles.* Springer-Verlag, Berlin, 2001.
3. American Psychiatric Association: *Diagnostic and Statistical Manual of Mental Disorders,* 4th Edition. Washington, D.C., Association, A.P., 1994.
4. Veggeberg, S. K. *The Major Mental Illnesses; Medications of the Mind.* Allen and Unwin Pty Ltd. St. Leonards, 1996, pp 68
5. Duinkerke, S. J.; Botter, P. A.; Jansen, A. A.; van Dongen, P. A.; van Haaften, A. J.; Boom, A. J.; van Laarhoven, J. H.; Busard, H. L. *Br. J. Psychiatry* 1993, 163, 451.
6. Tork, I. *Ann. N.Y. Acad. Sci.* 1990, 600, 9.
7. Prisco, S.; Pagannone, S.; Espsito, E. *J. Pharmacol. Exp. Ther.* 1994, 271.
8. Iyer, R. N.; Bradberry, C. W. *J. Pharmacol. Exp. Ther.* 1994, 271.
9. Gelders, Y. G. *Br. J. Psychiatry* 1989, 155, S33.
10. Rajagopalan, P. U.S. Pat. No. 5,321,023; 1994.
11. Rajagopalan, P. U.S. Pat. No. 4,438,120; 1984.
12. Blumberg, H. U.S. Pat. No. 3,790,675; 1974.
13. Adams, C. W. U.S. Pat. No. 3,983,123; 1976.
14. Yale, H. L.; Sowinski, F. A.; Bernstein, J. U.S. Pat. No. 3,133,936, 1964.
15. Margolis, B. J.; Swidorski, J. J.; Rogers, B. N. *J. Org. Chem.* 2003, 68, 644-647.
16. Pharmaceutical Manufacturing. In *Remington: The Science and Practice of Pharmacy.* Lippincott Williams & Wilkins, Philadelphia, 2005, 691-1058.
17. Weissig, V. *Liposomes: Methods and Protocols Volume 1: Pharmaceutical Nanocarriers.* Humana Press, New York, 2009.
18. Li, X. *Design of Controlled Release Drug Delivery Systems.* McGraw-Hill, New York, 2006.
19. Rautio, J. et al. Prodrugs: Design and Cinical Applications. *Nature Reviews Drug Discovery* 2008, 7, 255-270.

I claim:
1. A compound of Formula I, wherein

Formula I

A is —CH($R^9$)X—, —XCH($R^9$)—, —COX—, or —XCO—;
X is —O—, —S—, —SO—, or —$SO_2$—;
Y is a single bond or a double bond;
D and E are independently —$(CH_2)_n$—, and 'n' varies from 0 to 2;
$R^1$ is selected from the group consisting of hydrogen, $C_1$-$C_{10}$ alkyl, $C_1$-$C_{10}$ hydroxyalkyl, $C_1$-$C_{10}$ alkoxycarbonylalkyl, $C_5$-$C_{10}$ aryl, $C_6$-$C_{10}$ arylalkyl, and $C_6$-$C_{15}$ aroylalkyl;
each of $R^2$, $R^3$, $R^4$, $R^5$, $R^6$, $R^7$, $R^8$, and $R^9$ is independently selected from the group consisting of hydrogen, $C_1$-$C_{10}$ alkyl, hydroxyl, $C_1$-$C_{10}$ alkoxyl, —$NR^{10}R^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl, and $C_6$-$C_{10}$ arylalkyl; and
each of $R^{10}$ and $R^{11}$ is independently hydrogen or $C_1$-$C_{10}$ alkyl.

2. The compound of claim 1, wherein
A is —CH($R^9$)X—;
X is —O—, or —S—;
Y is a single bond or a double bond;
D and E are —$(CH_2)_n$—, and 'n' is 1;
$R^1$ is selected from the group consisting of hydrogen, $C_1$-$C_{10}$ alkyl, $C_1$-$C_{10}$ hydroxyalkyl, $C_1$-$C_{10}$ alkxoycarbonylalkyl, $C_5$-$C_{10}$ aryl, $C_6$-$C_{10}$ arylalkyl, and $C_6$-$C_{15}$ aroylalkyl;
each of $R^2$, $R^3$, $R^4$, $R^5$, $R^6$, $R^7$, $R^8$, and $R^9$ is independently selected from the group consisting of hydrogen, $C_1$-$C_{10}$ alkyl, hydroxyl, $C_1$-$C_{10}$ alkoxyl, —$NR^{10}R^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl, and $C_6$-$C_{10}$ arylalkyl; and
each of $R^{10}$ and $R^{11}$ is independently hydrogen or $C_1$-$C_{10}$ alkyl.

3. The compound of claim 2, wherein
X is —O—, or —S—;
Y is a double bond;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and
each of $R^4$ and $R^7$ is independently hydrogen, $C_1$-$C_{10}$ alkyl, or halogen.

4. The compound of claim 2, wherein
X is —O—, or —S—;
Y is a single bond;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and
each of $R^4$ and $R^7$ is independently hydrogen, $C_1$-$C_{10}$ alkyl, or halogen.

5. The compound of claim 3, wherein
$R^1$ is hydrogen, methyl or 3-(4-fluorobenzoyl)propyl; and
each of $R^2$, $R^3$, $R^4$, $R^5$, $R^6$, $R^7$, $R^8$, and $R^9$ is hydrogen.

6. The compound of claim 4, wherein
$R^1$ is hydrogen, methyl or 3-(4-fluorobenzoyl)propyl; and
each of $R^2$, $R^3$, $R^4$, $R^5$, $R^6$, $R^7$, $R^8$, and $R^9$ is hydrogen.

7. The compound of claim 1, wherein
A is —XCH($R^9$)—;
X is —O—, or —S—;
Y is a single bond or a double bond;
D and E are —$(CH_2)_n$—, and 'n' is 1;
$R^1$ is selected from the group consisting of hydrogen, $C_1$-$C_{10}$ alkyl, $C_1$-$C_{10}$ hydroxyalkyl, $C_1$-$C_{10}$ alkxoycarbonylalkyl, $C_5$-$C_{10}$ aryl, $C_6$-$C_{10}$ arylalkyl, and $C_6$-$C_{15}$ aroylalkyl;
each of $R^2$, $R^3$, $R^4$, $R^5$, $R^6$, $R^7$, $R^8$, and $R^9$ is independently selected from the group consisting of hydrogen, $C_1$-$C_{10}$ alkyl, hydroxyl, $C_1$-$C_{10}$ alkoxyl, —$NR^{10}R^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl, and $C_6$-$C_{10}$ arylalkyl; and
each of $R^{10}$ and $R^{11}$ is independently hydrogen or $C_1$-$C_{10}$ alkyl.

8. The compound of claim 7, wherein
X is —O—, or —S—;
Y is a double bond;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and each of $R^4$ and $R^7$ is independently hydrogen, $C_1$-$C_{10}$ alkyl, or halogen.

9. The compound of claim 7, wherein
X is —O—, or —S—;
Y is a single bond;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and
each of $R^4$ and $R^7$ is independently hydrogen, $C_1$-$C_{10}$ alkyl, or halogen.

10. The compound of claim 8, wherein
$R^1$ is hydrogen, methyl or 3-(4-fluorobenzoyl)propyl; and
each of $R^2$, $R^3$, $R^4$, $R^5$, $R^6$, $R^7$, $R^8$, and $R^9$ is hydrogen.

11. The compound of claim 9, wherein
$R^1$ is hydrogen, methyl or 3-(4-fluorobenzoyl)propyl; and
each of $R^2$, $R^3$, $R^4$, $R^5$, $R^6$, $R^7$, $R^8$, and $R^9$ is hydrogen.

12. A pharmaceutically acceptable drug product comprising compound of Formula I, Formula I wherein A is —CH($R^9$)X—, —XCH($R^9$)—, —COX—, or —XCO—;
X is —O—, —S—, —SO—, or —SO$_2$—;
Y is a single bond or a double bond;
D and E are independently —(CH$_2$)$_n$—, and 'n' varies from 0 to 2;
$R^1$ is selected from the group consisting of hydrogen, $C_1$-$C_{10}$ alkyl, $C_1$-$C_{10}$ hydroxyalkyl, $C_1$-$C_{10}$ alkoxycarbonylalkyl, $C_5$-$C_{10}$ aryl, $C_6$-$C_{10}$ arylalkyl, and $C_6$-$C_{15}$ aroylalkyl;
each of $R^2$, $R^3$, $R^4$, $R^5$, $R^6$, $R^7$, $R^8$, and $R^9$ is independently selected from the group consisting of hydrogen, $C_1$-$C_{10}$ alkyl, hydroxyl, $C_1$-$C_{10}$ alkoxyl, —NR$^{10}$R$^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl, and $C_6$-$C_{10}$ arylalkyl; and
each of $R^{10}$ and $R^{11}$ is independently hydrogen or $C_1$-$C_{10}$ alkyl.

13. The composition of claim 12, wherein
A is —CH($R^9$)X—;
X is —O—, or —S—;
Y is a single bond or a double bond;
D and E are —(CH$_2$)$_n$—, and 'n' is 1;
$R^1$ is selected from the group consisting of hydrogen, $C_1$-$C_{10}$ alkyl, $C_1$-$C_{10}$ hydroxyalkyl, $C_1$-$C_{10}$ alkxoycarbonylalkyl, $C_5$-$C_{10}$ aryl, $C_6$-$C_{10}$ arylalkyl, and $C_6$-$C_{15}$ aroylalkyl;
each of $R^2$, $R^3$, $R^4$, $R^5$, $R^6$, $R^7$, $R^8$, and $R^9$ is independently selected from the group consisting of hydrogen, $C_1$-$C_{10}$ alkyl, hydroxyl, $C_1$-$C_{10}$ alkoxyl, —NR$^{10}$R$^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl, and $C_6$-$C_{10}$ arylalkyl; and each of $R^{10}$ and $R^{11}$ is independently hydrogen or $C_1$-$C_{10}$ alkyl.

14. The drug product of claim 13, wherein
X is —O—, or —S—;
Y is a double bond;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and
each of $R^4$ and $R^7$ is independently hydrogen, $C_1$-$C_{10}$ alkyl, or halogen.

15. The composition of claim 13, wherein
X is —O—, or —S—;
Y is a single bond;
$R^1$ is hydrogen, $C_1$-$C_{10}$ alkyl, $C_6$-$C_{10}$ arylalkyl, or $C_6$-$C_{15}$ aroylalkyl;
each of $R^2$, $R^3$, $R^5$, $R^6$, $R^8$, and $R^9$ is hydrogen; and
each of $R^4$ and $R^7$ is independently hydrogen, $C_1$-$C_{10}$ alkyl, or halogen.

16. The composition of claim 14, wherein
X is —S—;
$R^1$ is hydrogen, methyl or 3-(4-fluorobenzoyl)propyl; and
each of $R^2$, $R^3$, $R^4$, $R^5$, $R^6$, $R^7$, $R^8$, and $R^9$ is hydrogen.

17. The composition of claim 15, wherein
X is —S—;
$R^1$ is hydrogen, methyl, or 3-(4-fluorobenzoyl)propyl; and
each of $R^2$, $R^3$, $R^4$, $R^5$, $R^6$, $R^7$, $R^8$, and $R^9$ is hydrogen.

18. A method of treating CNS disorders comprising administering an effective amount of pharmaceutically acceptable composition of Formula I, wherein Formula I A is —CH($R^9$)X—, —XCH($R^9$)—, —COX—, or —XCO—;
X is —O—, —S—, —SO—, or —SO$_2$—;
Y is a single bond or a double bond;
D and E are independently —(CH$_2$)$_n$—, and 'n' varies from 0 to 2;
$R^1$ is selected from the group consisting of hydrogen, $C_1$-$C_{10}$ alkyl, $C_1$-$C_{10}$ hydroxyalkyl, $C_1$-$C_{10}$ alkoxycarbonylalkyl, $C_5$-$C_{10}$ aryl, $C_6$-$C_{10}$ arylalkyl, and $C_6$-$C_{15}$ aroylalkyl;
each of $R^2$, $R^3$, $R^4$, $R^5$, $R^6$, $R^7$, $R^8$, and $R^9$ is independently selected from the group consisting of hydrogen, $C_1$-$C_{10}$ alkyl, hydroxyl, $C_1$-$C_{10}$ alkoxyl, —NR$^{10}$R$^{11}$, $C_1$-$C_{10}$ hydroxyalkyl, halogen, trihaloalkyl, cyano, carboxyl, $C_1$-$C_{10}$ acyl, $C_1$-$C_{10}$ alkxoyalkyl, $C_1$-$C_{10}$ alkxoycarbonyl, $C_5$-$C_{10}$ aryl, and $C_6$-$C_{10}$ arylalkyl; and
each of $R^{10}$ and $R^{11}$ is independently hydrogen or $C_1$-$C_{10}$ alkyl.

19. The method of claim 18, wherein
A is —CH($R^9$)X—;
X is —O—, or —S—;
Y is a single bond or a double bond;

D and E are —(CH$_2$)$_n$—, and 'n' is 1;

R$^1$ is selected from the group consisting of hydrogen, C$_1$-C$_{10}$ alkyl, C$_1$-C$_{10}$ hydroxyalkyl, C$_1$-C$_{10}$ alkxoycarbonylalkyl, C$_5$-C$_{10}$ aryl, C$_6$-C$_{10}$ arylalkyl, and C$_6$-C$_{15}$ aroylalkyl;

each of R$^2$, R$^3$, R$^4$, R$^5$, R$^6$, R$^7$, R$^8$, and R$^9$ is independently selected from the group consisting of hydrogen, C$_1$-C$_{10}$ alkyl, hydroxyl, C$_1$-C$_{10}$ alkoxyl, —NR$^{10}$R$^{11}$, C$_1$-C$_{10}$ hydroxyalkyl, halogen, trihaloalkyl, cyano, carboxyl, C$_1$-C$_{10}$ acyl, C$_1$-C$_{10}$ alkxoyalkyl, C$_1$-C$_{10}$ alkxoycarbonyl, C$_5$-C$_{10}$ aryl, and C$_6$-C$_{10}$ arylalkyl; and each of R$^{10}$ and R$^{11}$ is independently hydrogen or C$_1$-C$_{10}$ alkyl.

20. The method of claim 19, wherein

X is —O—, or —S—;

Y is a double bond;

R$^1$ is hydrogen, C$_1$-C$_{10}$ alkyl, C$_6$-C$_{10}$ arylalkyl, or C$_6$-C$_{15}$ aroylalkyl;

each of R$^2$, R$^3$, R$^5$, R$^6$, R$^8$, and R$^9$ is hydrogen; and each of R$^4$ and R$^7$ is independently hydrogen, C$_1$-C$_{10}$ alkyl, or halogen.

21. The method of claim 19, wherein

X is —O—, or —S—;

Y is a single bond;

R$^1$ is hydrogen, C$_1$-C$_{10}$ alkyl, C$_6$-C$_{10}$ arylalkyl, or C$_6$-C$_{15}$ aroylalkyl;

each of R$^2$, R$^3$, R$^5$, R$^6$, R$^8$, and R$^9$ is hydrogen; and each of R$^4$ and R$^7$ is independently hydrogen, C$_1$-C$_{10}$ alkyl, or halogen.

22. The method of claim 20, wherein

R$^1$ is hydrogen, methyl or 3-(4-fluorobenzoyl)propyl; and each of R$^2$, R$^3$, R$^4$, R$^5$, R$^6$, R$^7$, R$^8$, and R$^9$ is hydrogen.

23. The method of claim 21, wherein

R$^1$ is hydrogen, methyl or 3-(4-fluorobenzoyl)propyl; and each of R$^2$, R$^3$, R$^4$, R$^5$, R$^6$, R$^7$, R$^8$, and R$^9$ is hydrogen.

24. The method of claim 18, wherein

A is —XCH(R$^9$)—;

X is —O—, or —S—;

Y is a single bond or a double bond;

D and E are —(CH$_2$)$_n$—, and 'n' is 1;

R$^1$ is selected from the group consisting of hydrogen, C$_1$-C$_{10}$ alkyl, C$_1$-C$_{10}$ hydroxyalkyl, C$_1$-C$_{10}$ alkxoycarbonylalkyl, C$_5$-C$_{10}$ aryl, C$_6$-C$_{10}$ arylalkyl, and C$_6$-C$_{15}$ aroylalkyl;

each of R$^2$, R$^3$, R$^4$, R$^5$, R$^6$, R$^7$, R$^8$, and R$^9$ is independently selected from the group consisting of hydrogen, C$_1$-C$_{10}$ alkyl, hydroxyl, C$_1$-C$_{10}$ alkoxyl, —NR$^{10}$R$^{11}$, C$_1$-C$_{10}$ hydroxyalkyl, halogen, trihaloalkyl, cyano, carboxyl, C$_1$-C$_{10}$ acyl, C$_1$-C$_{10}$ alkxoyalkyl, C$_1$-C$_{10}$ alkxoycarbonyl, C$_5$-C$_{10}$ aryl, and C$_6$-C$_{10}$ arylalkyl; and each of R$^{10}$ and R$^{11}$ is independently hydrogen or C$_1$-C$_{10}$ alkyl.

25. The method of claim 24, wherein

X is —O—, or —S—;

Y is a double bond;

R$^1$ is hydrogen, C$_1$-C$_{10}$ alkyl, C$_6$-C$_{10}$ arylalkyl, or C$_6$-C$_{15}$ aroylalkyl;

each of R$^2$, R$^3$, R$^5$, R$^6$, R$^8$, and R$^9$ is hydrogen; and each of R$^4$ and R$^7$ is independently hydrogen, C$_1$-C$_{10}$ alkyl, or halogen.

26. The method of claim 24, wherein

X is —O—, or —S—;

Y is a single bond;

R$^1$ is hydrogen, C$_1$-C$_{10}$ alkyl, C$_6$-C$_{10}$ arylalkyl, or C$_6$-C$_{15}$ aroylalkyl;

each of R$^2$, R$^3$, R$^5$, R$^6$, R$^8$, and R$^9$ is hydrogen; and each of R$^4$ and R$^7$ is independently hydrogen, C$_1$-C$_{10}$ alkyl, or halogen.

27. The method of claim 25, wherein

R$^1$ is hydrogen, methyl or 3-(4-fluorobenzoyl)propyl; and each of R$^2$, R$^3$, R$^4$, R$^5$, R$^6$, R$^7$, R$^8$, and R$^9$ is hydrogen.

28. The method of claim 26, wherein

R$^1$ is hydrogen, methyl or 3-(4-fluorobenzoyl)propyl; and each of R$^2$, R$^3$, R$^4$, R$^5$, R$^6$, R$^7$, R$^8$, and R$^9$ is hydrogen.

\* \* \* \* \*